United States Patent [19]

Talley

[11] Patent Number: 4,503,270

[45] Date of Patent: Mar. 5, 1985

[54] METHOD OF PRODUCING 2,3,6 TRIMETHYLPHENOL

[75] Inventor: John J. Talley, Clifton Park, N.Y.

[73] Assignee: General Electric Company, Schenectady, N.Y.

[21] Appl. No.: 553,659

[22] Filed: Nov. 21, 1983

[51] Int. Cl.$^3$ .................... C07C 37/46; C07C 39/06
[52] U.S. Cl. .................................. 568/783; 568/716
[58] Field of Search ........................... 568/716, 783

[56] References Cited

U.S. PATENT DOCUMENTS

| | | | |
|---|---|---|---|
| 3,880,837 | 4/1975 | Kamoshita et al. | 568/783 |
| 4,103,096 | 7/1978 | Giolito et al. | 568/783 |

FOREIGN PATENT DOCUMENTS

| | | | |
|---|---|---|---|
| 93329 | 8/1974 | Japan | 568/783 |

OTHER PUBLICATIONS

Braddeley, "J. Chem. Soc.", vol. 994, pp. 527–531, (1950).
Fury et al., "J. Org. Chem.", vol. 30, pp. 2301–2304, (1965).

*Primary Examiner*—Werren B. Lone
*Attorney, Agent, or Firm*—Richard J. Traverso; James C. Davis, Jr.; James Magee, Jr.

[57] ABSTRACT

A method is provided for producing 2,3,6 trimethylphenol by rearrangement of 2,4,6 trimethylphenol in the presence of an aluminum based catalyst, such as AlCl$_3$, and an acid upon heating the mixture to a temperature within the range of 80° C. to 150° C.

29 Claims, No Drawings

METHOD OF PRODUCING 2,3,6 TRIMETHYLPHENOL

BACKGROUND OF THE INVENTION

This invention relates to a method of producing intermediate structures from the rearrangement of alkylated phenols in the presence of an aluminum based catalyst. More particularly, this invention relates to the rearrangment of 2,4,6 trimethylphenol to provide 2,3,6-trimethylphenol in the presence of an aluminum based catalyst.

The ability to rearrange certain alkylated phenols, other than 2,4,6 trimethylphenol, in the presence of excess aluminum chloride has been disclosed by Baddeley, J. CHEM. SOC. Vol. 994, pp. 527–531 (1950). Baddeley does not achieve complete rearrangement of all the starting material in his process. The starting materials remain in equilibrium with the finished products, making the product yields low.

Fury and Pearson, J. Org. Chem. Vol. 30, pp. 2301–2304 (1965), disclose that complete rearrangment of the alkylated phenol starting material can be achieved by introducing anhydrous hydrogen chloride to the reaction medium with excess aluminum chloride. However, they do not obtain desirable reaction intermediates as finished products in the process they disclose. For example, Fury and Pearson disclose that the only product obtained upon rearrangement of 2,4,6 trimethylphenol is 2,3,5 trimethylphenol. They do not obtain 2,3,6 trimethylphenol from the rearrangment of 2,4,6 trimethylphenol and they do not indicate that such a product can be obtained.

This invention is based on the discovery that intermediate structures, such as 2,3,6 trimethylphenol, are produced in the rearrangement of certain methylated phenols, such as 2,4,6 trimethylphenol, and that these intermediate structures can be isolated from the reaction medium in high yields by controlling the rate of the rearrangement reaction. It has also been discovered that anhydrous hydrogen chloride need not be added to the reaction medium to obtain complete conversion of starting materials and high yields of intermediates where the reaction vessel is maintained under pressure and an acid generating catalyst is used.

SUMMARY OF THE INVENTION

The method of producing 2,3,6 trimethylphenol is provided by heating 2,4,6 trimethylphenol in the presence of of an aluminum based catalyst at a temperature in the range of about 80° C. to about 150° C. under pressure. Where the aluminum based catalyst is an organometallic catalyst, an anhydrous protonic acid is added to the reaction medium.

OBJECTS OF THE INVENTION

An object of the present invention is to produce 2,3,6 trimethylphenol in high yields with little or no by-product.

Another object of the present invention is to rearrange 2,4,6 trimethylphenol to a more useful compound.

Another object of the present invention is to rearrange substantially all of an alkylated phenol in the presence of an aluminum halide catalyst without the addition of anhydrous hydrogen chloride or other protonic acid to the reaction medium.

STATEMENT OF THE INVENTION

These objects and other objects of this invention are accomplished by introducing an anhydrous aluminum based catalyst preferably to a quantity of 2,4,6 trimethylphenol (2,4,6-TMP), the molar quantity of anhydrous aluminum based catalyst being equal to or greater than the number of moles of 2,4,6 trimethylphenol. The reaction mixture is then heated to the desired reaction temperature and the pressure is maintained at the desired value to obtain 2,3,6 trimethylphenol (2,3,6-TMP). The reaction will also produce a quantity of 2,3,5 trimethylphenol (2,3,5-TMP) from the 2,3,6 trimethylphenol initially produced. Essentially two rearrangements can occur within the reaction mixture.

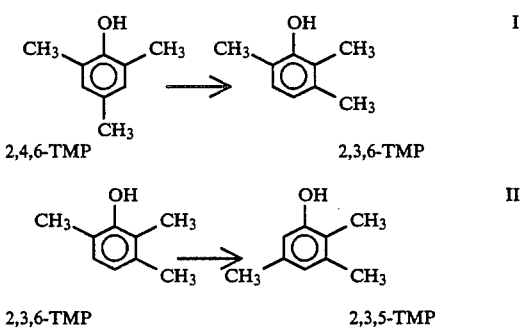

There is no equilibrium obtained for the rearrangement of 2,3,6 trimethylphenol to 2,3,5 trimethylphenol. To obtain any 2,3,6 trimethylphenol from the reaction mixture described above, the reaction must be interrupted before all the 2,4,6 trimethylphenol is converted to 2,3,5 trimethylphenol.

To obtain high yields of 2,3,6 trimethylphenol, the time at which the reaction must be interrupted is dependent upon the rate of rearrangement in the reaction mixture. The rate of reaction is dependent on factors such as, for example, the quantity of aluminum based catalyst, the quantity of anhydrous protonic acid which is dissolved in the reaction mixture, the concentration of 2,4,6 trimethylphenol starting material, the reaction temperature, the type of aluminum based catalyst utilized, the type of anhydrous protonic acid dissolved in the reaction mixture, etc.

To avoid complete conversion to 2,3,5-TMP the reaction should not continue beyond twenty four hours, even at very low reaction temperatures (80° C.). The preferred duration of the reaction is actually less than three hours. After three hours within the most preferred temperature range (120° C.–130° C.), all the 2,4,6 trimethylphenol has typically rearranged and the 2,3,6 trimethylphenol produced has been slowly rearranging to 2,3,5 trimethylphenol for most of this time. Under conditions which favor high rates of rearrangement, the conversion of 2,4,6 trimethylphenol to 2,3,6 trimethylphenol is complete within minutes. The production of 2,3,6 trimethylphenol is believed to begin instantaneously under conditions conducive to rearrangement and once produced, a portion of the 2,3,6 trimethylphenol begins to rearrange to 2,3,5 trimethylphenol immediately.

The term "aluminum based catalyst" as used herein is intended to describe and include the members of a group of catalysts consisting of aluminum halide catalysts, $AlX_3$, such as aluminum chloride, aluminum bromide and aluminum iodide and the organometallic catalysts of the formula $RAlX_2$, wherein X is a halogen from the group consisting of chlorine, bromine and iodine and R is a monovalent organic radical selected from the group consisting of alkyl radicals of from 1 to 20 carbon atoms and aromatic radicals of from 6 to 20 carbon atoms. The term "aluminum based catalyst" is also intended to describe and include mixtures of the catalysts in the group described above.

For the aluminum based catalysts to function, they must be in the presence of an anhydrous protonic acid. The aluminum halide catalysts will provide rearrangement of 2,4,6 trimethylphenol without the addition of an anhydrous protonic acid since such an acid is generated in the reaction mixture upon the addition of the aluminum halide catalyst to the 2,4,6 trimethylphenol in accordance with the following equation.

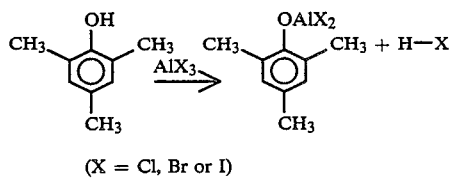

(X = Cl, Br or I)

The reaction mixture must be maintained under pressure to prevent the acid from escaping.

The organometallic catalysts of the formula $RAlX_2$ require the addition of an anhydrous protonic acid to the reaction mixture to achieve rearrangement of 2,4,6 trimethylphenol since an acid is not generated upon reaction of the organometallic catalyst and the 2,4,6 trimethylphenol.

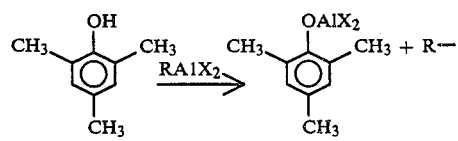

(X = Cl, Br or I, R = as defined above)

Instead the reaction provides an organic compound from the monovalent organic radical that dissociates from the organometallic catalyst.

The term "protonic acid" as used herein is intended to describe hydrogen compounds which dissociate in water and provide a free proton, $H^+$ or $H_3^+O$. Essentially any protonic acid is suitable for activating the aluminum based catalysts utilized in this invention to provide rearrangement of 2,4,6 trimethylphenol. However, some of these acids may react with the 2,4,6 trimethylphenol and produce an unwanted derivative. For example, sulfuric acid can cause the addition of a sulfonate radical to the 2,4,6 trimethylphenol and nitric acid can cause the nitration of 2,4,6 trimethylphenol.

Protonic acids that are preferred for addition to the reaction medium are those that are generated by the reaction of aluminum halide catalyst and the 2,4,6 trimethylphenol. These include, hydrogen chloride, hydrogen bromide and hydrogen iodide. Other protonic acids which are suitable include the following:
HF—Hydrogen fluoride
$HClO_4$—Perchloric
$HClO_3$—Chloric
$HClO_2$—Chlorous
HClO—Hypochlorous
$HBrO_3$—Bromic
$H_2CO_3$—Carbonic
$H_3PO_2$—Hypophosphorous
$H_3PO_3$—Phosphorous
$H_3PO_4$—Phosphoric Carboxylic acids are also suitable such as, for example, acetic acid, formic acid, propanoic acid, butanoic acid, 2-methyl propanoic acid, pentanoic acid, chloroacetic acid, trichloroacetic acid, trifluoroacetic acid, stearic acid, benzoic acid, phenyl acetic acid, 2-chlorobutanoic,3-chlorobutanoic dichloroacetic acid, palmitic acid, 4-chlorobutanoic acid, 5-chlorobutanoic acid, etc.

To obtain a significant degree of rearrangement, it is preferable to utilize a molar quantity of aluminum based catalyst which exceeds the molar quantity of 2,4,6 trimethylphenol. Where the quantity of catalyst falls below 1 molar equivalent of 2,4,6 trimethylphenol, negligible rearrangement occurs even at preferred reaction temperatures over relatively long reaction times.

Not wishing to be bound by theory, it is believed that one equivalent of the aluminum based catalyst is necessary to react with the hydroxyl group of the 2,4,6 trimethylphenol and provide the species in which rearrangement takes place, as illustrated in Equations III and IV. The quantity of catalyst which falls above 1 molar equivalent of 2,4,6 trimethylphenol is then free to initiate rearrangement. The quantity of catalyst above 1 molar equivalent is believed to form a complex with the anhydrous protonic acid generated or introduced into the reaction medium in accordance with the following equations:

$$RAlX_2 + 2(H-Z) \rightarrow R-H + HAlX_2Z_2 \quad \text{V}$$

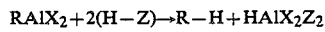

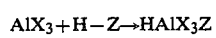

wherein X is selected from a group consisting of chlorine, bromine and iodine, R is an organic radical as previously defined and Z is the conjugate base of a suitable protonic acid. It is believed these complexes (Lewis acids) provide a proton which rearranges the methyl groups on the 2,4,6 trimethylphenol.

The preferred quantity of catalyst falls in the range of one to two moles per mole of 2,4,6 trimethylphenol. Only a trace quantity of aluminum based catalyst above 1 molar equivalent of 2,4,6 TMP is necessary to obtain a high rate of rearrangement. Quantities of catalyst larger than 2 molar equivalents of 2,4,6 trimethylphenol can be utilized; however, the rate of rearrangement is very high and the quantity of 2,3,5 trimethylphenol produced is very large.

Where an anhydrous protonic acid is to be added to the reaction medium and it is a gas at the reaction temperature, it is either bubbled through the reaction mixture or the reaction mixture is maintained under a fixed pressure of the protonic acid gas. Maintaining the reaction medium under pressure of the anhydrous protonic acid is preferred since a smaller quantity of acid can be used and this quantity can be monitored and controlled.

It is preferable to maintain the pressure of the reaction medium within the range of about 5–70 psig to keep the protonic acid in solution. This range is preferred where the protonic acid is generated in the reaction medium and where it is introduced. Where the protonic acid is generated in the reaction medium, the pressures may be generated by another gas so long as the protonic acid remains in solution. Where excessive acid is produced, the gaseous anhydrous acid may be released to maintain the pressure desired.

Although a protonic acid is generated within the reaction mixture upon addition of an aluminum halide catalyst, additional amounts of acid may be introduced if higher pressures are desired to maintain more acid in solution.

The use of pressures of anhydrous protonic acid above 30 psig are preferred over those below 30 psig since the rate of rearrangement is relatively low. However, quantities above 70 psig of anhydrous protonic acid acclerate the rearrangement reaction and produce large quantities of 2,3,5 trimethylphenol. Although these high pressures can be utilized, they are not preferred for the production of 2,3,6 trimethylphenol.

The temperature of the reaction mixture during rearrangement is preferably maintained within the range of about 80° C. to about 150° C. Temperatures higher than 150° C. produce larger quantities of 2,3,5 trimethylphenol than is desirable due to a higher rate of rearrangement. At temperatures below 80° C., the rate of 2,4,6 trimethylphenol rearrangement is very low, even after extended periods of exposure to such temperatures. The most preferred temperatures fall in the range of about 120° C. to 130° C.

The rate of rearrangement can also be reduced by reducing the concentration of the reactants. This is accomplished by introducing a solvent to the reaction medium. Suitable solvents include any aprotic solvent such as, for example, chlorobenzene, benzene, toluene, dichlorobenzene, chloroform, etc. Solvents containing amino groups or hydroxy groups are unsuitable since they interfere with the catalyst. As indicated above, chlorinated hydrocarbon and unsubstituted hydrocarbon solvents are suitable. The concentration of 2,4,6 trimethylphenol in solvent can fall as low as 0.01 moles per liter of solvent. Since the reaction can proceed in the absence of solvent, the upper limit of the concentration of 2,4,6 trimethylphenol in solvent approaches 100%. High yields of 2,3,6 trimethylphenol have been obtained where the 2,4,6 trimethylphenol is maintained at a concentration of one mole/liter of solvent and such a concentration is preferred over more dilute concentrations to avoid the use of large quantities of solvent.

Once the reaction proceeds, the rearrangement is stopped by the addition of water to hydrolize the aluminum based catalyst. Where a solvent is utilized and the reaction conditions have been maintained in the preferred ranges discussed above, a reaction time of about 10 minutes is preferred. However, as discussed above, 2,3,6 trimethylphenol can be obtained at both longer and shorter reaction times. It has been found that yields of 2,3,6 trimethylphenol suffer significantly after three hours when operating at the most preferred reaction conditions.

The following examples are provided so that those skilled in the art may better understand this invention. It is not intended to limit the scope of the invention to the embodiments they describe.

EXAMPLES 1-9

In each of examples 1-9, the following procedure was utilized. Details as to the reaction conditions and the reaction products for each of the examples is reported in Table I.

A 200 ml. Fisher-Porter pressure bottle was charged with 2,4,6 trimethylphenol and anhydrous AlCl$_3$ in a quantity corresponding to that reported in Table I. The bottle was equipped with a pressure regulator and then charged with anhydrous hydrogen chloride to a pressure as specified in Table I for the particular example. No special precautions were taken to exclude atmospheric moisture. The vessel was then placed in oil bath at a temperature as indicated in Table I. The reaction mixture typically became homogeneous and acquired a red color. The reaction was maintained at the temperature specified in Table I and the rearrangement reaction was interrupted by pouring the reaction mixture over 300 ml. of ice water. The aqueous phase with precipitated product was extracted with methylene chloride. The combined methylene chloride abstract was washed with saturated aqueous sodium bicarbonate and then passed through a plug of glass wool. The methylene chloride was removed on a rotary evaporator to isolate the product.

The weight percent of 2,4,6 trimethylphenol, 2,3,6 trimethylphenol, and 2,3,5 trimethylphenol which appeared in the product are shown in Table I.

TABLE I

Rearrangement of 2,4,6 Trimethylphenol with AlCl$_3$ and HCl

| Example | Temp °C. | Reaction Time (min) | Molar equiv. AlCl$_3$ | HCl psig | Products (wt. %) | | |
|---|---|---|---|---|---|---|---|
| | | | | | 2,4,6* | 2,3,6* | 2,3,5* |
| 1 | 124 | 180 | 2.0 | 50 | 1.5 | 1.3 | 97.2 |
| 2 | 124 | 50 | 2.0 | 50 | 1.2 | 18.3 | 80.6 |
| 3 | 124 | 10 | 2.0 | 50 | 1.4 | 38.1 | 59.5 |
| 4 | 124 | 60 | 0.0 | 50 | 100.0 | 0.0 | 0.0 |
| 5 | 120 | 60 | 0.75 | 50 | 70.9 | 9.0 | 10.3 |
| 6 | 120 | 60 | 1.0 | 50 | 66.2 | 18.9 | 7.8 |
| 7 | 80 | 60 | 2.0 | 50 | 37.9 | 39.7 | 18.0 |
| 8 | 105 | 120 | 2.0 | 50 | 5.5 | 30.1 | 59.2 |
| 9 | 110 | 45 | 2.0 | 50 | 3.7 | 53.6 | 37.1 |

*Trimethylphenol

Examples 1-3 illustrate the effect the reaction time has on the yield of 2,3,6 trimethylphenol. All reaction conditions in these three examples were maintained the same except for the reaction time. Where the reaction time was three hours, the reaction product was essentially 2,3,5 trimethylphenol. In Example 1, over 97% of the 2,4,6 trimethylphenol started with was rearranged to 2,3,5 trimethylphenol. Example 2 indicates how a reduction in reaction time substantially increases the yield of 2,3,6 trimethylphenol. Example 3 indicates how short reaction times are essential in obtaining high yields of 2,3,6 trimethylphenol when operating in the most preferred temperature range. The yield of 2,3,6 trimethylphenol was doubled by reducing the reaction time from 50 to 10 minutes.

Examples 4-6 demonstrate the importance of utilizing 1 mole of aluminum based catalyst. In Example 5, less than 1 molar equivalent of AlCl$_3$ was utilized and only 30% of the 2,4,6 trimethylphenol rearranged after one hour. Increasing the quantity of of AlCl$_3$ to 1 mole per mole of 2,4,6 trimethylphenol did not significantly enhance the rate of rearrangement, as shown in Example 6.

Examples 7-9 illustrate the role that the reaction temperature plays in determining the rate of rearrangement. Only a portion of the 2,4,6 trimethylphenol rearranged where the reaction temperature was maintained at 80° C., even though the reaction was permitted to proceed for one hour. Examples 8 and 9 illustrate that high yields of 2,3,6 trimethylphenol can be obtained for relatively long reaction times where lower reaction temperatures are utilized. For example, although the reaction was permitted to proceed for two hours in Example 8, a higher yield of 2,3,6 trimethylphenol was obtained over that of Example 2, which operated at 124° C. Example 9 illustrates how the low temperatures and short reaction times can be utilized in concert to obtain high yields of 2,3,6 trimethylphenol. In this example, the highest yield of 2,3,6 trimethylphenol was obtained.

EXAMPLES 10-14

In each of examples 10-14, the same procedure was followed as described in examples 1-9. All reaction parameters were kept relatively constant at values similar to those in examples 1-9 except the reaction time. All reaction times were below 50 minutes. Details as to the reaction parameters and the product yield for each example are reported in Table II.

TABLE II

Rearrangement of 2,4,6 Trimethylphenol With AlCl₃ and HCl

| Example | Temp °C. | Reaction Time (Min) | Molar Equiv. AlCl₃ | HCl psig | Products wt. % 2,4,6* | 2,3,6* | 2,3,5* | Others |
|---|---|---|---|---|---|---|---|---|
| 10 | 110 | 15 | 2 | 45 | 21.9 | 53.8 | 23.4 | 0.0 |
| 11 | 110 | 15 | 2 | 50 | 3.2 | 57.4 | 35.6 | 1.1 |
| 12 | 110 | 20 | 2 | 50 | 3.9 | 57.1 | 36.8 | 1.5 |
| 13 | 110 | 25 | 2 | 50 | 6.6 | 52.7 | 38.2 | 1.9 |
| 14 | 110 | 45 | 2 | 50 | 3.7 | 53.6 | 37.1 | 0.0 |

*Trimethylphenol

EXAMPLES 15-23

In each of examples 15-23, the same procedure was followed as described in examples 1-9 except that a solvent, dichlorobenzene, was added to the 2,4,6 trimethylphenol starting material. The concentration of 2,4,6 trimethylphenol for each of example 145-23 is specified in Table III along with all reaction parameters and product yields.

TABLE III

Rearrangement of 2,4,6 Trimethylphenol in Chlorobenzene

| Example | Temp °C. | Reaction Time (Min.) | Conc. of 2,4,6*(Molarity) | HCl psig | Molar equiv. AlCl₃ | Products wt % 2,4,6* | 2,3,6* | 2,3,5* | Others |
|---|---|---|---|---|---|---|---|---|---|
| 15 | 124 | 11.5 | 2.1 | 40 | 2.0 | 67.3 | 23.7 | 9.0 | — |
| 16 | 130 | 25 | 2.1 | 45 | 1.5 | 4.5 | 54.9 | 38.0 | 2.6 |
| 17 | 130 | 30 | 1.5 | 45 | 1.5 | 3.5 | 51.0 | 43.4 | 2.1 |
| 18 | 100 | 30 | 2.0 | 42 | 2.0 | 3.5 | 51.0 | 43.4 | 2.2 |
| 19 | 100 | 60 | 2.0 | 40 | 2.0 | 8.7 | 62.6 | 28.0 | 0.8 |
| 20 | 85 | 60 | 2.0 | 35 | 1.5 | 49.4 | 34.5 | 15.7 | 0.4 |
| 21 | 85 | 180 | 2.0 | 35 | 1.5 | 12.1 | 62.3 | 25.6 | — |
| 22 | 85 | 225 | 2.0 | 35 | 1.5 | 19.4 | 56.4 | 23.5 | 0.7 |
| 23 | 85 | 960 | 2.0 | 35 | 1.5 | 8.8 | 63.7 | 26.8 | 0.6 |

*Trimethylphenol

EXAMPLE 24

This example illustrates that a sufficient quantity of a protonic acid can be generated within the reactor so as not to require any additional acid.

To a 10-gallon glass-lined reactor equipped with a reverse curve impeller, baffles and thermocouple probe were added in order 7.54 Kg 2,4,6 trimethylphenol, 15.1 L chlorobenzene, and 11.31 Kg aluminum chloride. The reactor was sealed and heated in an oil bath. The pot temperature rose steadily to 120° C. over 110 minutes, during which time six samples were collected and analyzed by introducing the sample to ice water, extracting the product and solvent with methylene chloride and distilling off the methylene chloride and chlorobenzene. No anhydrous protonic acid was introduced. In fact, anhydrous HCl was vented off the reaction vessel to maintain a pressure below 40 psig. The composition of each of the six samples analyzed is shown in Table IV.

TABLE IV

Rearrangement of 2,4,6 Trimethylphenol in Chlorobenzene without HCl

| Sample | Reaction Time (Min) | Products wt % 2,4,6* | 2,3,6* | 2,3,5* | Others |
|---|---|---|---|---|---|
| 1 | 29 | 81.0 | 13.6 | 4.8 | — |
| 2 | 44 | 56.5 | 27.0 | 15.4 | — |
| 3 | 55 | 27.8 | 43.5 | 26.8 | 1.5 |
| 4 | 70 | 12.8 | 48.5 | 36.6 | 2.0 |
| 5 | 85 | 7.6 | 44.3 | 44.8 | 3.0 |
| 6 | 110 | 6.0 | 37.9 | 54.0 | 3.0 |

*Trimethylphenol

EXAMPLE 25

This example also illustrates that a protonic acid need not be introduced into a reaction mixture where an alumium halide catalyst is used. To a 200 ml Fisher-Porter pressure bottle were added (100 gms) 2,4,6 trimethylphenol and (50 gms) of anhydrous AlCl₃. The bottle was equipped with a pressure regulator to monitor the pressure of HCl produced. No HCl was added. The vessel was placed in an oil bath and heated to 130° C. A pressure of 60 psig was noted. The reaction was interrupted after 40 minutes by adding the reaction mixture to 300 ml of ice water. The product was extracted with methylene chloride which was evaporated off to isolate the product. The product comprised 34.0 weight percent 2,4,6 trimethylphenol, 37.1 weight percent 2,3,6 trimethylphenol and 26.8 weight percent 2.35 trimethylphenol with the remainder being byproducts.

Although the above examples have shown various modifications of the present invention, further modifications are possible in light of the above techniques by one skilled in the art without departing from the scope and spirit of this invention.

What is claimed is:

1. A method of producing 2,3,6 trimethylphenol comprising heating 2,4,6 trimethylphenol in the presence of an aluminum halide catalyst at a temperature in the range of about 80° C. to about 150° C. under pressure.

2. A method as in claim 1 wherein the quantity of aluminum halide catalyst is in the range of about 1.0 to 10.0 molar equivalents of 2,4,6 trimethylphenol.

3. A method as in claim 2 wherein the pressure falls within the range of about 5 to 70 psig.

4. A method as in claim 3 wherein the temperature is maintained within the range of about 110° C. to 130° C. for a period of 3 hours or less.

5. A method as in claim 3 wherein the aluminum halide catalyst is aluminum chloride.

6. A method as in claim 3 wherein the quantity of aluminum halide catalyst is about 1 to 2 molar equivalents of 2,4,6 trimethylphenol.

7. A method as in claim 3 wherein the 2,4,6 trimethylphenol and aluminum halide catalyst is heated for about 60 minutes or less.

8. A method as in claim 1 wherein the 2,4,6 trimethylphenol is in the presence of an aprotic solvent.

9. A method as in claim 8 wherein the quantity of aluminum halide catalyst is in the range of about 1.0 to 10.0 molar equivalents of 2,4,6 trimethylphenol.

10. A method as in claim 9 wherein the pressure falls within the range of about 5 to 70 psig.

11. A method as in claim 10 wherein the temperature is maintained within the range of 110° to 130° C. for a period of 3 hours or less.

12. A method as in claim 10 wherein the quantity of aluminum halide catalyst falls within the range of about 1 to 2 molar equivalents of 2,4,6 trimethylphenol.

13. A method as in claim 10 wherein the 2,4,6 trimethylphenol, aluminum halide catalyst and aprotic solvent are heated for 24 hours or less.

14. A method as in claim 10 wherein the aluminum halide catalyst is aluminum chloride.

15. A method as in claim 8 wherein the aprotic solvent is selected from the group consisting of chlorobenzene, dichlorobenzene, toluene, benzene, methylene chloride and chloroform.

16. A method as in claim 15 wherein the concentration of 2,4,6 trimethylphenol within said aprotic solvent falls within the range of 0.1 molar to 2.5 molar.

17. A method of producing 2,3,6 trimethylphenol comprising heating a solution of 2,4,6 trimethylphenol in a concentration in the range of about 0.1 to 2.5 molar in the presence of about 1.0 to 2.0 molar equivalents of aluminum chloride under a pressure in the range of about 5 to 30 psig at a temperature in the range of about 110° C. to about 130° C. for a period of about 25 to 70 minutes, said solvent being selected from the group consisting of chlorobenzene, dichlorobenzene, toluene, benzene, methylene chloride and chloroform.

18. A method of producing 2,3,6 trimethylphenol comprising heating 2,4,6 trimethylphenol in the presence of an aluminum based catalyst and an anhydrous protonic acid at a temperature in the range of about 80° C. to about 150° C.

19. A method as in claim 18 wherein the 2,4,6 trimethylphenol, aluminum based catalyst and anhydrous protonic acid are maintained under pressure of anhydrous protonic gas in the range of about 5 to about 70 psig during heating.

20. A method as in claim 19 wherein the protonic acid is selected from the group consisting of hydrogen chloride, hydrogen bromide, hydrogen iodide, hydrogen fluoride, perchloric acid, chloric acid, chlorous acid, hypoclorous acid, boric acid, carbonic acid, hypophosphorous acid, phosphorous acid, phosphoric acid, acetic acid, butanoic acid, propanoic acid, formic acid, 2-methyl propanoic acid, pentanoic acid, chloroacetic acid, trichloroacetic acid, trifluoroacetic acid, stearic acid, benzoic acid, phenyl acetic acid, 2 chlorobutanoic acid, 3-chlorobutanoic acid, 4-chlorobutanoic acid and 5-chlorobutanoic acid.

21. A method as in claim 20 wherein the aluminum based catalyst is selected from the group consisting of aluminum chloride, aluminum bromide and aluminum iodide.

22. A method as in claim 20 wherein the quality of aluminum based catalyst is maintained within the range of 1 to 2 molar equivalents and 2,4,6 trimethylphenol.

23. A method as in claim 20 wherein the heating period is limited to 24 hours or less.

24. A method as in claim 20 wherein the pressure of anhydrous protonic acid is maintained at about 30 psig and the temperature is maintained at about 110° C. to about 130° C. for a period of about 3 hours or less.

25. A method as in claim 20 wherein the 2,4,6 trimethylphenol is in the presence of an aprotic solvent.

26. A method as in claim 25 wherein the aprotic solvent is selected from the group consisting of chlorobenzene, dichlorobenzene toluene, benzene, methylene chloride and chloroform.

27. A method as in claim 25 wherein the concentration of 2,4,6 trimethylphenol within said aprotic solvent is within the range of 0.1 molar to 2.5 molar.

28. A method as in claim 25 wherein the temperature is maintained within the range of 110° to 130° C., the pressure of anhydrous protonic acid is maintained within the range of about 30 to 50 psig and the reaction time is maintained at about 80 minutes or less.

29. A method of producing 2,3,6 trimethylphenol comprising heating 2,4,6 trimethylphenol in the presence of an aprotic solvent, 1.0 to 2.0 molar equivalents of aluminum chloride, 5 to 50 psig of anhydrous hydrogen chloride gas at a temperature in the range of 110° to 130° C. for 80 minutes or less; said aprotic solvent being selected from the group consisting of chlorobenzene, dichlorobenzene, chloroform, toluene, methylene chloride and benzene and said concentration of 2,4,6 trimethylphenol falling within the range of 0.1 to 2.5 molar.

* * * * *